United States Patent
Balshi

(10) Patent No.: US 9,351,922 B2
(45) Date of Patent: May 31, 2016

(54) COMPOSITION FOR CORRECTING SKIN PIGMENT CONDITIONS

(71) Applicant: Thomas Christopher Balshi, Delray Beach, FL (US)

(72) Inventor: Thomas Christopher Balshi, Delray Beach, FL (US)

( * ) Notice: Subject to any disclaimer, the term of this patent is extended or adjusted under 35 U.S.C. 154(b) by 0 days.

(21) Appl. No.: 14/186,780

(22) Filed: Feb. 21, 2014

(65) Prior Publication Data

US 2014/0170091 A1 Jun. 19, 2014

Related U.S. Application Data

(63) Continuation-in-part of application No. 13/712,594, filed on Dec. 12, 2012, now abandoned.

(51) Int. Cl.

| A61K 8/97 | (2006.01) |
|---|---|
| A61K 8/27 | (2006.01) |
| A61K 8/60 | (2006.01) |
| A61K 8/49 | (2006.01) |
| A61Q 19/02 | (2006.01) |
| A61Q 17/04 | (2006.01) |
| A61K 8/67 | (2006.01) |
| A61K 8/37 | (2006.01) |
| A61Q 19/00 | (2006.01) |

(52) U.S. Cl.
CPC ... *A61K 8/97* (2013.01); *A61K 8/27* (2013.01); *A61K 8/37* (2013.01); *A61K 8/602* (2013.01); *A61K 8/675* (2013.01); *A61K 8/676* (2013.01); *A61Q 19/02* (2013.01); *A61Q 17/04* (2013.01); *A61Q 19/00* (2013.01)

(58) Field of Classification Search
USPC .............. 424/59, 725, 729, 744, 758; 514/42
See application file for complete search history.

(56) References Cited

U.S. PATENT DOCUMENTS

| 6,024,942 | A | 2/2000 | Tanner et al. | |
|---|---|---|---|---|
| 7,842,723 | B2 | 11/2010 | Gupta | |
| 2004/0166069 | A1 | 8/2004 | Gupta | |
| 2009/0016971 | A1 * | 1/2009 | Gaudry et al. | ................. 424/45 |
| 2009/0169608 | A1 | 7/2009 | Ziegler et al. | |
| 2011/0206793 | A1 | 8/2011 | Hines et al. | |
| 2011/0229536 | A1 | 9/2011 | Kvitnitsky et al. | |
| 2012/0128606 | A1 | 5/2012 | Igiebor et al. | |
| 2012/0157939 | A1 | 6/2012 | Loy et al. | |

FOREIGN PATENT DOCUMENTS

| WO | WO 94/07460 | * | 4/1994 | |
|---|---|---|---|---|
| WO | 2004/043422 A1 | | 5/2004 | |
| WO | WO 2004043422 A1 | * | 5/2004 | ............. A61K 8/673 |
| WO | WO 2009/063491 | * | 5/2009 | |

OTHER PUBLICATIONS

Personal Care Magazine online article "Novel enhancing silicone copolymer introduced," dated Jun. 2009.*

* cited by examiner

*Primary Examiner* — Ileana Popa
*Assistant Examiner* — Alissa Prosser
(74) *Attorney, Agent, or Firm* — O'Rourke Law Office, LLC

(57) ABSTRACT

The present invention relates to a composition that provides for skin pigment correction comprising: zinc oxide; octinoxate; α-arbutin; ascorbic acid; glycyrrhiza glabra extract; green tea extract; pomegranate extract; cucumber extract; niacinamide; and a carrier. The composition can be used to treat a variety of pigment issues including lentigo, liver spots, melasma, post-inflammatory pigment issues, sun spots, freckles, and age spots.

6 Claims, No Drawings

COMPOSITION FOR CORRECTING SKIN PIGMENT CONDITIONS

CROSS-REFERENCE TO RELATED APPLICATION

This application is a continuation-in-part application of U.S. patent application Ser. No. 13/712,594 filed Dec. 12, 2012, the disclosure of which is incorporated by reference as if fully set forth herein.

FIELD OF THE INVENTION

The embodiments described herein relate to novel compositions for correcting skin pigment conditions in a mammal (particularly a human) in need of such pigment correction.

DESCRIPTION OF RELATED ART

A useful pigment correcting composition must have at least two properties. First, the active ingredients therein must provide for correction of a pigment condition (e.g., liver spots). Second, the composition should desirably provide protection against UV radiation so as to prevent the UV radiation from undoing and/or limiting the pigment correction done by the pigment correcting agents.

The literature has put forth several formulations for sunscreen compositions. These include:

Published Patent Application Number US 2012/0128606 which describes a variety of skin products including a Skin Beautifying Milk, Body Creme, Fade Creme and MaxiTone;

Published Patent Application Number US 2009/0169608 which describes a topically applicable composition for use as a skin bleaching agent;

U.S. Pat. No. 7,842,723 which describes ascorbic acid— natural sugar lactone esters for comprehensive skin and scalp care;

Published Patent Application Number US 2011/0229536 which describes compositions for topical applications comprising microencapsulated colorants;

Published Patent Application Number US 2012/0157939 which describes compositions comprising lilium siberia extracts and uses thereof;

Published Patent Application Number US 2004/0166069 which describes boosting tyrosinase inhibiting activity of skin whitening and sunscreen compositions;

U.S. Pat. No. 6,024,942 which describes photoprotective compositions;

Published PCT Application WO 2004/043422 which describes an improved cosmetic composition;

Published U.S. Patent Application Number US 2011/0206793 which describes topical skin care formulation;

These compositions, however, do not provide for pigment correction as disclosed herein. There is also a fundamental difference between sunscreens and pigment correcting compositions. Sunscreens are designed for wide-area application on the human body to protect the skin from UV radition. In contrast, a pigment correcting composition is applied to an area in need of pigment correction and not over the entire body. In short, none of these references describe the embodiments described herein.

SUMMARY OF THE INVENTION

It is an object of the embodiments described herein to provide a composition for correcting skin pigment conditions. The instant composition can be used as a face or a body cream. In addition, the composition can be used to treat various skin pigment conditions including lentigo, liver spots, melasma, post-inflammatory pigment issues, sunspots, freckles, and age spots. In use, the composition is applied to the skin area in need of pigment correction.

In a preferred embodiment, the composition for correcting skin pigment conditions comprises zinc oxide; octinoxate; α-arbutin; ascorbic acid; glycyrrhiza glabra extract; green tea extract; pomegranate extract; cucumber extract; niacinamide; and a carrier. In a preferred embodiment, α-arbutin is present in a range of from: 0.5%-2% by weight; ascorbic acid is present in a range of from 0.25%-2% by weight; green tea extract is present in a range of from 0.05-0.25% by weight; glycyrrhiza glabra extract is present in a range from 0.10%-0.5% by weight, and niacinamide is present in a range of from 0.025%-0.25% by weight. In a most preferred embodiment, α-arbutin is present at 1.25% by weight; ascorbic acid is present at 0.50% by weight; green tea extract is present at 0.10% by weight; glycyrrhiza glabra extract is present at 0.25% by weight; and niacinamide is present at 0.05% by weight.

In the most preferred embodiment, the composition for correcting skin pigment conditions comprises zinc oxide; octinoxate; α-arbutin; aloe barbadensis leaf juice; water; ascorbic acid; bis-vinyl dimethicone copolymer; camellia sinensis leaf (green tea) extract; C13-14 isoparaffin; caprylic/capric triglyceride; cucumis sativus fruit extract; cyclomethicone; dimethicone; ethylhexylglycerin; glycerin; glyceryl stearate; glycyrrhiza glabra extract; helianthus annuus oil; laureth-7; niacinamide; parfum; PEG-100 stearate; phenoxyethanol; polyacrylamide; polysorbate-20; punica granatum (pomengranate) extract; and tocopheryl acetate.

In a preferred embodiment, α-arbutin is present in a range of from: 0.5%-2% by weight; ascorbic acid is present in a range of from 0.25%-2% by weight; green tea extract is present in a range of from 0.05-0.25% by weight; glycyrrhiza glabra is present in a range of from 0.10%-0.5% by weight, and niacinamide is present in a range of from 0.025%-0.25% by weight. In a most preferred embodiment, α-arbutin is present at 1.25% by weight; ascorbic acid is present at 0.50% by weight; green tea extract is present at 0.10% by weight; glycyrrhiza glabra extract is present at 0.25% by weight; and niacinamide is present at 0.05% by weight.

The present invention also includes a method of correcting a pigment issue comprising applying a composition for correcting a skin pigment condition to the skin of a person in need of pigment correction, said composition comprising zinc oxide; octinoxate; α-arbutin; ascorbic acid; glycrrhiza glabra extract; green tea extract; pomegranate extract; cucumber extract; niacinamide; and a carrier. In a preferred embodiment, α-arbutin is present in a range of from: 0.5%-2% by weight; ascorbic acid is present in a range of from 0.25%-2% by weight; green tea extract is present in a range of from 0.05-0.25% by weight; glycyrrhiza glabra extract is present in a range of from 0.10%-0.5% by weight, and niacinamide is present in a range of from 0.025%-0.25% by weight. In a most preferred embodiment, α-arbutin is present at 1.25% by weight; ascorbic acid is present at 0.50% by weight; green tea extract is present at 0.10% by weight; glycyrrhiza glabra extract is present at 0.25% by weight; and niacinamide is present at 0.05% by weight.

The pigment issues that can be corrected include liver spots, melasma and post-inflammatory pigment issues.

In its most preferred embodiment, the method of correcting a pigment issue comprises applying a composition for correcting a skin pigment condition to the skin of a mammal and, most preferably, a person in need of pigment correction, said composition comprising: zinc oxide; octinoxate; α-arbutin; aloe barbadensis leaf juice; water; ascorbic acid; bis-vinyl dimethicone copolymer; camellia sinensis leaf (green tea) extract; C13-14 isoparaffin; caprylic/capric triglyceride; cucumis sativus fruit extract; cyclomethicone; dimethicone; ethylhexylglycerin; glycerin; glyceryl stearate; glycyrrhiza glabra extract; helianthus annuus oil; laureth-7; niacinamide; parfum; PEG-100 stearate; phenoxyethanol; polyacrylamide; polysorbate-20; punica granatum (pomegranate) extract; and tocopheryl acetate. In a preferred embodiment, α-arbutin is present in a range of from: 0.5%-2% by weight; ascorbic acid is present in a range of from 0.25%-2% by weight; green tea extract is present in a range of from 0.05-0.25% by weight; glycyrrhiza glabra is present in a range of from 0.10%-0.5% by weight, and niacinamide is present in a range of from 0.025%-0.25% by weight. In a most preferred embodiment, α-arbutin is present at 1.25% by weight; ascorbic acid is present at 0.50% by weight; green tea extract is present at 0.10% by weight; glycyrrhiza glabra extract is present at 0.25% by weight; and niacinamide is present at 0.05% by weight.

DETAILED DESCRIPTION OF THE PREFERRED EMBODIMENTS

Any suitable carrier may be used in the compositions of the embodiments described herein. Preferably, for a skin care composition, the carrier is a cosmetically-acceptable carrier. As will be recognized by those of skill in the art, cosmetically acceptable carriers comprise carriers that are suitable for use in contact with the body, in particular the skin, for pigment correcting application, without undue toxicity, incompatibility, instability, irritation, allergic response, and the like.

The carrier can be in a wide variety of forms. For example, emulsion carriers, including, but not limited to, oil-in-water, water-in-oil, water-in-oil-in-water, and oil-in-water-in-silicone emulsions. The emulsions can cover a wide range of viscosities.

Examples of suitable cosmetically-acceptable carriers include cosmetically-acceptable solvents and materials for cosmetic solutions, suspensions, lotions, creams, serums, essences, gels, toners, sticks, sprays, ointments, liquid washes and soap bars, shampoos, hair conditioners, pastes, foams, mousses, powders, shaving creams, wipes, patches, strips, powdered patches, microneedle patches, bandages, hydrogels, film-forming products, facial and skin masks, make-up, liquid drops, and the like. These product types may contain several types of cosmetically-acceptable carriers including, but not limited to solutions, suspensions, emulsions such as microemulsions and nanoemulsions, gels, solids, liposomes, other encapsulation technologies and the like. The formulation of an acceptable carrier is within the skill of those in the art.

In a preferred embodiment, the composition has a SPF rating of 15. The SPF rating can be adjusted.

Although the invention has been described with respect to specific embodiments, it is not intended to be limited thereto and various modifications which will become apparent to the person of ordinary skill in the art are intended to fall within the spirit and scope of the invention as described herein taken in conjunction with the appended claims.

What is claimed is:

1. A composition for correcting a skin pigment condition consisting of:
   zinc oxide;
   octinoxate;
   α-arbutin;
   aloe barbadensis leaf juice;
   water;
   ascorbic acid;
   bis-vinyl dimethicone copolymer;
   camellia sinensis leaf (green tea) extract;
   C13-14 isoparaffin;
   caprylic/capric triglyceride;
   cucumis sativus fruit extract;
   cyclomethicone;
   dimethicone;
   ethylhexylglycerin;
   glycerin;
   glyceryl stearate;
   glycyrrhiza glabra extract;
   helianthus annuus oil;
   laureth-7;
   niacinamide;
   parfum;
   PEG-100 stearate;
   phenoxyethanol;
   polyacrylamide;
   polysorbate-20;
   punica granatum extract; and
   tocopheryl acetate;
   wherein α-arbutin is present in a range of 0.5%-2% by weight; ascorbic acid is present in a range of 0.25%-2% by weight; green tea extract is present in a range of 0.05-0.25% by weight; glycyrrhiza glabra extract is present in a range of 0.10%-0.5% by weight, and niacinamide is present in a range of 0.025%-0.25% by weight.

2. The composition of claim 1, wherein α-arbutin is present at 1.25% by weight; ascorbic acid is present at 0.50% by weight; green tea extract is present at 0.10% by weight; glycyrrhiza glabra extract is present at 0.25% by weight; and niacinamide is present at 0.05% by weight.

3. A method of correcting a skin pigment condition comprising applying a composition for correcting a pigment condition to the skin of a person in need of pigment correction, said composition consisting of:
   zinc oxide;
   octinoxate;
   α-arbutin;
   aloe barbadensis leaf juice;
   water;
   ascorbic acid;
   bis-vinyl dimethicone copolymer;
   camellia sinensis leaf (green tea) extract;
   C13-14 isoparaffin;
   caprylic/capric triglyceride;
   cucumis sativus fruit extract;
   cyclomethicone;
   dimethicone;
   ethylhexylglycerin;
   glycerin;
   glyceryl stearate;
   glycyrrhiza glabra extract;
   helianthus annuus oil;
   laureth-7;
   niacinamide;
   parfum;
   PEG-100 stearate;
   phenoxyethanol;
   polyacrylamide;
   polysorbate-20;
   punica granatum extract; and
   tocopheryl acetate;

wherein α-arbutin is present in a range of 0.5%-2% by weight; ascorbic acid is present in a range of 0.25%-2% by weight; green tea extract is present in a range of 0.05-0.25% by weight; glycyrrhiza glabra extract is present in a range of 0.10%-0.5% by weight, and niacinamide is present in a range of 0.025%-0.25% by weight.

4. The method of claim 3, wherein the pigment condition is a liver spot.

5. The method of claim 3, wherein the pigment condition is melasma.

6. The method of claim 3, wherein the pigment condition is a post-inflammatory pigment condition.

\* \* \* \* \*